(12) United States Patent
Welch et al.

(10) Patent No.: US 6,399,607 B1
(45) Date of Patent: Jun. 4, 2002

(54) AMINOMETHYLENE AMIDE ANALOGS OF PYRAZINAMIDE WITH INTRACELLULAR ANTIMYCOBACTERIAL ACTIVITY AGAINST PYRAZINAMIDE-RESISTANT MYCOBACTERIA COMBINED WITH A RIFAMYCIN

(75) Inventors: John T. Welch, Albany, NY (US); Leonid B. Heifets, Denver, CO (US); Michael H. Cynamon, Dewitt, NY (US)

(73) Assignee: Research Foundation-State University of New York, Rensselaer, NY (US)

( * ) Notice: Subject to any disclaimer, the term of this patent is extended or adjusted under 35 U.S.C. 154(b) by 0 days.

(21) Appl. No.: 09/607,893

(22) Filed: Jun. 30, 2000

Related U.S. Application Data (60) Provisional application No. 60/142,268, filed on Jul. 2, 1999.

(51) Int. Cl.⁷ ............... A61K 31/50; A61K 31/70; A61K 31/495
(52) U.S. Cl. ............... 514/247; 514/31; 514/252.1
(58) Field of Search ............... 514/247, 252.1, 514/31

(56) References Cited

U.S. PATENT DOCUMENTS

| | | | |
|---|---|---|---|
| 3,108,099 A | * 10/1963 | Felder et al. | 514/252 |
| 4,962,111 A | * 10/1990 | Welch et al. | |
| 5,643,912 A | * 7/1997 | Cynamon et al. | 514/255 |

OTHER PUBLICATIONS

Derivati basici dell'acido pirazin–2–carbonico ad azione antimicobactterica, F. Bonati, Minerva Medica, pp. 1704–1708.

* cited by examiner

*Primary Examiner*—Kevin E. Weddington
(74) *Attorney, Agent, or Firm*—Heslin Rothenberg Farley & Mesiti P.C.; Mary Louise Gioeni (57) ABSTRACT

Methods for treating diseases involving pyrazinamide-resistant mycobacteria comprise administering to a mammal in need of treatment a therapeutically effective amount of a combination of rifamycin and a compound of formula I:

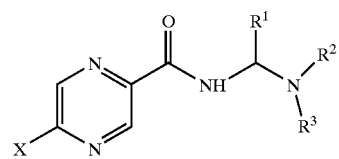

wherein
  $R^1$ is hydrogen haloalkyl, or lower alkyl;
  $R^2$ and $R^3$ are independently chosen from alkyl, substituted alkyl, cycloalkyl, aryl, substituted aryl, alkylaryl and substituted alkylaryl, or $R^2$ and $R^3$ taken together form a five- or six-membered heterocyclic or substituted heterocyclic ring; and
  X is hydrogen, halogen, or lower alkyl;
or a pharmaceutically acceptable salt thereof.

19 Claims, 2 Drawing Sheets

AMINOMETHYLENE AMIDE ANALOGS OF PYRAZINAMIDE WITH INTRACELLULAR ANTIMYCOBACTERIAL ACTIVITY AGAINST PYRAZINAMIDE-RESISTANT MYCOBACTERIA COMBINED WITH A RIFAMYCIN

This appln claims benefit of Provisional Appln Ser. No. 60/142,268 Jun. 2, 1999.

BACKGROUND OF THE INVENTION

Tuberculosis is a contagious disease caused by *Mycobacterium tuberculosis* (Mtb). The primary areas of infection are the lungs, and the lower respiratory region. The infection occurs by airborne transmission of droplet nuclei containing viable, virulent organisms produced by sputum-positive individuals. The bacilli are then deposited in the alveolar spaces of the lungs, where they are engulfed by alveolar macrophages. Once the tubercle bacilli enter the air sacs of the lungs, they multiply and spread throughout the body through the blood stream. A portion of the infectious inoculum resists intracellular destruction in the macrophage, persisting and eventually multiplying and killing the macrophage. The disease develops in individuals whose immune system is unable to successfully destroy the initial infection, and is characterized by symptoms such as chronic cough, low grade fever, night sweats and weight loss. A world wide epidemic of Tuberculosis currently exists. Incidence of the disease roughly correlates with poor economic conditions in particular geographic areas, with the highest incidence in developing countries. Improving social and sanitary conditions and ensuring adequate nutrition are necessary components to strengthen the body's defenses against the tubercle bacillus. Tuberculosis is also found to be prevalent in people infected with HIV. A significant factor contributing to Tuberculosis resurgence is the emergence of multi-drug resistant organisms. Failure to complete the full course of drug therapy can lead to *Mycobacterium tuberculosis* (Mtb) organisms that are resistant to one or more anti-tuberculosis drugs, severely limiting effective treatment options. Mtb is a rod shape bacillus that favors high oxygen tissue tension and a neutral pH for growth. Mtb has also demonstrated slow and periodic growth in test studies as well as a susceptibility to acidic pH, inside phagolysosomes of macrophages. The organism exists in different metabolic states corresponding to different tissue environments. Actively growing extracellular organisms make up the largest population of mycobacteria. A second environment is inside the macrophages, at acid pH, where the organisms grow slowly. A third environment is in solid carouse areas, at neutral pH, where the organism also grows slowly. Another bacterial population, considered truly dormant, cannot be inhibited by any drug, and may therefore be susceptible only to the host's own cellular defense mechanisms.

Pyrazinamide (PZA) is one of the few effective anti-tuberculosis drugs used in therapy. It is a white crystalline powder with a $pK_a$ of 0.5 and a molecular weight of 123.11 g/mole, and formula $C_6H_7NO$. First synthesized by Hall and Spoerri in 1940, Yeager and associates reported the antimicrobial activity of the compound in 1952.

While PZA is active against so-called susceptible strains of Mtb, it is not active against strains that have developed resistance to PZA. (A morpholine derivative of PZA, morphazinamide (MZA) has been used as an anti-tuberculosis drug, but is not reported to be effective against resistant strains.) Neither is it active against the closely related organism *Mycobacterium avium*. (Heifets et al, *Am. Rev. Resp. Dis.* 134: 1287–1288 (1986). *M. avium* has become a serious cause of disseminated infection among patients with AIDS. *M. kansasii* is another disease-causing mycobacterium that is resistant to PZA. PZA is also not effective against Mtb organisms which have been phagocytized. For example, PZA has been found to be either weakly or clearly bacteriostatic in macrophages, with a reduced efficacy after 4 to 7 days.

The antibacterial activity of PZA has been related to the formation of pyrazinoic acid (POA), which is formed by the action of the enzyme pyrazinamidase. One postulated mechanism for the resistance of Mtb to pyrazinamide is based on the ability of the organism to suppress formation of pyrazinamidase. Antimycobacterial activity of PZA is pH-dependent with greater efficacy at lower pH. This pH dependence may be related to POA formation.

Therefore there is a need for an effective anti mycobacterial drug having activity against PZA-resistant Mtb, against *M. avium*, and against phagocytized organisms and having activity over a broad range of pH values.

SUMMARY OF INVENTION

Surprisingly, it has been found that amides of pyrazine-2-carboxylic acid display good activity against *M. avium*, PZA-resistant *M. tuberculosis*, and phagocytized *M. tuberculosis*, and these compounds also show activity over a broad range of pH values.

In one aspect, the present invention relates to a method for treating for treating diseases involving pyrazinamide-resistant mycobacteria, including tuberculosis involving pyrazine-resistant or phagocytized *Mycobacterium tuberculosis*, and diseases caused by *Mycobacterium avium* and *Mycobacterium kansasii*. The method comprises administering to a mammal in need of treatment a therapeutically effective amount of a compound of formula

I wherein
$R^1$ is hydrogen haloalkyl, or lower alkyl;
$R^2$ and $R^3$ are independently chosen from alkyl, substituted alkyl, cycloalkyl, aryl, substituted aryl, alkylaryl and substituted alkylaryl, or $R^2$ and $R^3$ taken together form a five- or six-membered heterocyclic or substituted heterocyclic ring with nitrogen;
X is hydrogen, halogen, lower alkyl or $-NR^4R^5$; and
$R^4$ and $R^5$ are independently lower alkyl or cycloalkyl, or $R^4$ and $R^5$ taken together form a five- or six-membered heterocyclic or substituted heterocyclic ring with nitrogen;

or a pharmaceutically acceptable salt thereof. The activity of the compounds of formula I against mycobacteria is independent of pH.

In another aspect, the present invention relates to pharmaceutical compositions comprising a compound of formula 1, or a pharmaceutically acceptable salt thereof.

DETAILED DESCRIPTION OF THE INVENTION

Figure 1:
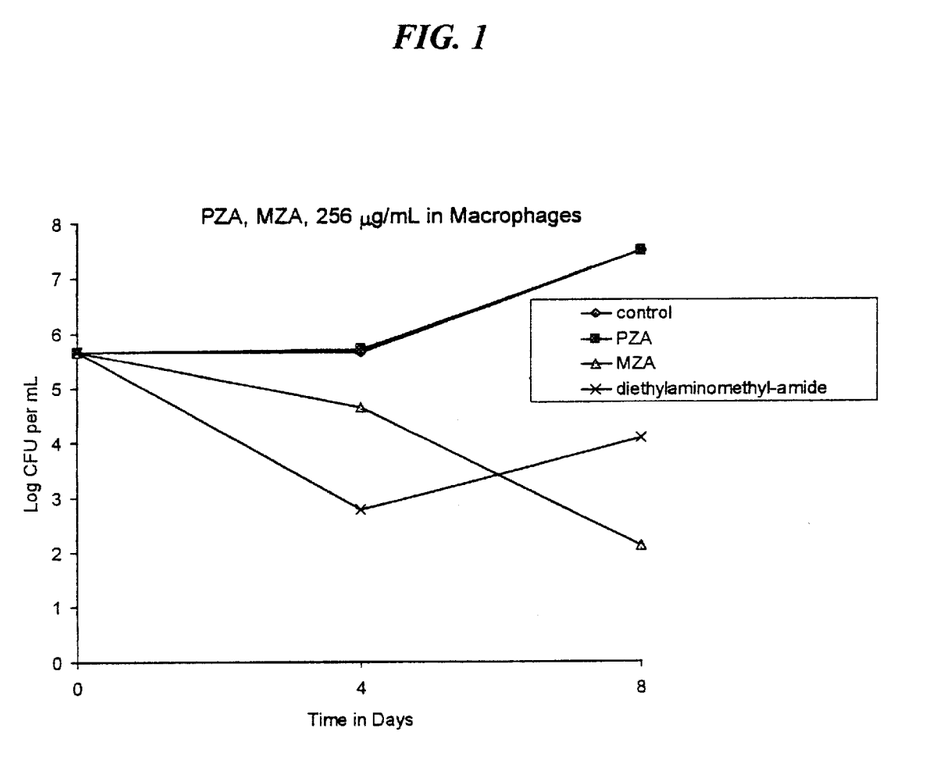
FIG. 1 is a plot showing reduction of infection by PZA-resistant Mtb in macrophages (as measured by number of colony forming units (CFU)) by compounds of formula I, in comparison to a control and to PZA.
Figure 2:
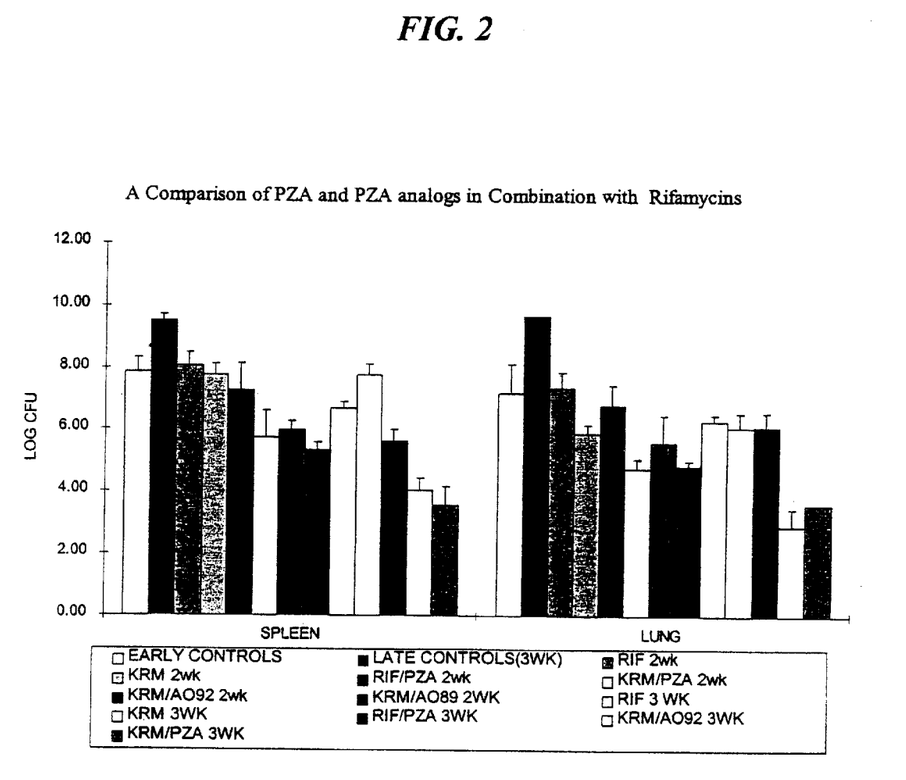
FIG. 2 is a bar chart showing the reduction of Mtb infection by compounds of formula I in an animal model.

The active ingredient of the methods and compositions of the present invention is a compound of formula I:

wherein
- $R^1$ is hydrogen haloalkyl, or lower alkyl;
- $R^2$ and $R^3$ are independently chosen from alkyl, substituted alkyl, cycloalkyl, aryl, substituted aryl, alkylaryl and substituted alkylaryl, or $R^2$ and $R^3$ taken together form a five- or six-membered heterocyclic or substituted heterocyclic ring with nitrogen;
- X is hydrogen, halogen, lower alkyl or $-NR^4R^5$; and
- $R^4$ and $R^5$ are independently lower alkyl or cycloalkyl, or $R^4$ and $R^5$ taken together form a five- or six-membered heterocyclic or substituted heterocyclic ring with nitrogen.

In a preferred embodiment, $R^2$ and $R^3$ are independently chosen from alkyl, aryl, and alkylaryl, or $R^2$ and $R^3$ taken together form a five- or six-membered heterocyclic ring chosen from morpholine, piperadine, piperazine, pyrrolidine and substituted piperazine.

Compounds of formula I that are preferred for the compositions and methods of the present invention are listed in Table 1.

TABLE 1

1

2

3

TABLE 1-continued

4

5

6

7

8

9

10

11

TABLE 1-continued

The compounds may be prepared by the method exemplified below.

In the context of the present invention, alkyl is intended to include linear, branched, or cyclic hydrocarbon structures and combinations thereof. Lower alkyl refers to alkyl groups of from to 4 carbon atoms. Examples of lower alkyl groups include methyl, ethyl, propyl, isopropyl, butyl, s-and t-butyl. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, and norbornyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Aryl and heteroaryl mean a 5- or 6-membered aromatic or heteroaromatic ring containing 0–3 heteroatoms selected from nitrogen, oxygen or sulfur; a bicyclic 9- or 10-membered aromatic or heteroaromatic ring system containing 0–3 heteroatoms selected from Nitrogen, oxygen or sulfur; or a tricyclic 13- or 14-membered aromatic or heteroaromatic ring system containing 0–3 heteroatoms selected from Nitrogen, oxygen or sulfur. Each of these rings is optionally substituted with 1–3 lower alkyl, substituted alkyl, substituted alkynyl, carbonyl, nitro, halogen, haloalkyl, hydroxy, alkoxy, $OCH(COOH)_2$, cyano, primary amino, secondary amino, acylamino, phenyl, benzyl, phenoxy, benzyloxy, heteroaryl, or heteroaryloxy; each of said phenyl, benzyl, phenoxy, benzyloxy, heteroaryl, and heteroaryloxy is optionally substituted with 1–3 substitutents selected from lower alkyl, alkenyl, alkynyl, halogen, hydroxy, haloalkyl, alkoxy, cyano, phenyl, benzyl, benzyloxy, carboxamido, heteroaryl, heteroaryloxy, nitro or —NRR (where in R is independently H, lower alkyl or cycloalkyl, and —RR may be fused to form a cyclic ring with nitrogen). The aromatic 6- to 14-membered carbocyclic rings include, for example, benzene, naphthalene, indane, tetralin, and fluorene; and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Alkylaryl means an alkyl residue attached to an aryl ring. Examples are benzyl and phenethyl. Heteroarylalkyl means an alkyl residue attached to a heteroaryl ring. Examples include pyridinylmethyl and pyrimidinylethyl.

Heterocycle means a cycloalkyl or aryl residue in which one to two of the carbons is replaced by a heteroatom such as oxygen, nitrogen or sulfur. Examples of heterocycles that fall within the scope of the invention include pyrrolidine, piperadine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted alkyl, aryl, cycloalkyl, or heterocyclyl refer to alkyl, aryl, cycloalkyl, or heterocyclyl wherein up to three H atoms in each residue are replaced with halogen, haloalkyl, hydroxy, lower alkoxy, carboxy, carboalkoxy, carboxamido, cyano, carbonyl, nitro, primary amino, secondary amino, alkylthio, sulfoxide, sulfone, acylamino, amidino, phenyl, benzyl, heteroaryl, phenoxy, benzyloxy, heteroaryloxy, or substituted phenyl, benzyl, heteroaryl, phenoxy, benzyloxy, or heteroaryloxy.

The present invention encompasses a method for treating diseases involving pyrazinamide-resistant mycobacterium. These diseases include tuberculosis involving pyrazinamide-resistant *Mycobacterium tuberculosis*, and phagocytized *Mycobacterium tuberculosis* and also diseases caused by *Mycobacterium avium* or *M. kansasii*.

In another aspect, the present invention relates to a pharmaceutical composition comprising a compound of formula I, or a pharmaceutically acceptable salt thereof. In a preferred embodiment, the composition also contains a pharmaceutically acceptable carrier.

The pharmaceutical compositions containing the active ingredient may be in a form suitable for oral use, for example as tablets, aqueous or oily suspensions, dispersible powders or granules, emulsions, hard or soft capsules. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia, and lubricating agents, for example magnesium stearate, stearic acid or talc. The tablets may be uncoated or they may be coated by known techniques to delay disintegration and absorption in the gastrointestinal tract and thereby provide sustained action over a longer period.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth, and gum acacia; dispersing or wetting agents may be a naturally-occurring phosphatide, for example lecithin or condensation products of alkylene oxide with fatty acids, for example polyoxyethylene stearate, or condensation products of ethylene oxide with long chain aliphatic alcohols, for example heptadecethyleneoxycetanol, or condensation products of ethylene oxide with partial ester derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxy benzoate, one or more coloring agents, one or more flavoring agents, and one or more sweetening agents such as sucrose or saccharin.

Oily suspensions may be formulated by suspending the active ingredient in a vegetable oil, for example such as arachis oil, olive oil, sesame oil or coconut oil, or in a mineral oil such as liquid paraffin. The oil suspensions may contain thickening agents, for example beeswax, hard paraffin or cetyl alcohol. Sweetening agents such as those set forth above, and flavoring agents may be added to provide a palatable oral preparation. These compositions may be preserved by addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present. The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleates. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. The suspension may be formulated according to the known art using those suitable dispersing and wetting agents and suspending agents which have been mentioned above. The sterile injectable preparation may also be a sterile injectable solution or suspension in a non-toxic parenterally-acceptable diluent or solvent, for example as a solution in 1,3-butanediol. Among acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid find use in the preparation of injectibles.

EXAMPLES

Example 1

General Synthesis for Compounds Without Nuclear Pyrazine Substitution

To a 10 mL round-bottom flask containing 0.99 g of pyrazinamide was added 2.6 mL of diethyl amine and 1 mL of formalin. The reaction mixture was heated to 95–100° C. for 5 hours then was concentrated in vacuo. The residue was elutriated with hot hexane and the hexane fractions were combined. Following evaporation of the hexane fractions, the residue was purified by recrystallization from hot hexane to yield the desire product in nearly 90% yield. (Yield pyrrolidine example 30%) Other analogs are more readily elutriated with benzene or benzene hexane mixtures.

Example 2

Synthesis for Compounds with Nuclear Pyrazine Substitution

To a 10 mL round-bottom flask, containing 0.31 g of 5-chloro-pyrazinamide was added 0.2 mL of diethyl amine and 0.3 mL of formalin. The reaction mixture was heated to 95–100° C. for 5 hours then was concentrated in vacuo. The residue was elutriated with hot benzene and the benzene fractions were combined. Following evaporation of the hexane fractions, the residue was purified by recrystallization from hot hexane to yield the desired product in nearly 90% yield.

Biological Evaluation

Methods employed for biological evaluation of the compounds were as follows: Stock solutions were prepared by dissolving each compound in modified 7H10 broth (7H10 agar formulation with agar and malachite green omitted), pH 5.8, with 10% oleic acid-albumin-dextrose-cattalos (OADC) enrichment (Difco Laboratories, Detroit, Mich.) at a concentration 2048 mg per mL. Stock solutions were sterilized by passage through a 0.22 mm pore size membrane filter. Stock solutions of PA and 5-Cl PA were adjusted to pH 5.8 with 1 N KOH prior to sterilization Mycobacteria were grown in modified 7H10 broth, pH 6.6 with 10% OADC enrichment and 0.05% Tween 80. Cell suspensions were diluted in modified 7H10 broth, pH 5.8 to yield 1 Klett unit/mL of *M. tuberculosis, M. bovis, M. smegmatis* and 0.1 Klett unit/mL of *M. avium*, and *M. kansasii*. inoculum size was determined by titration and counting from duplicate 7H10 agar plates. The minimum inhibitory concentration (MIC) of the experimental compounds was determined. MIC is defined as the lowest concentration of drug which produced no visible turbidity after a period of time.

Example 3

Activity of selected amides of pyrazine carboxylic acid of formula I against pyrazinamide-resistant strains of *M. tuberculosis* was evaluated. An MIC was determined for each compound. Table 2 shows the activity of various compounds against the strains of *M. tuberculosis* shown. In the table, ATCC 27294 is H37RV, a strain susceptible to pyrazinamide treatment, ATCC 35822 is an isoniazid (INH)-resistant strain, ATCC35828 is a PZA resistant strain and MS6210 is a resistant clinical isolate from National Jewish Hospital, Denver, Colo.

TABLE 2

MICs of Pyrazinamide Analogs v. resistant *M. tuberculosis*

| | *M. tuberculosis* | | | |
|---|---|---|---|---|
| Pyrazinoic Acid Amide | MS 6210 | ATCC 27294 | ATCC 35822 | ATCC 35828 |
| PZA | 100 | 33 | 33 | >300 |
| (morpholin-4-ylmethyl)-amide (4) | 100 | 100 | 33 | 100 |
| dipropylaminomethyl-amide (9) | 100 | 100 | 100 | 100 |
| (piperazin-1-ylmethyl)-amide (7) | 100 | 300 | 100 | 300 |
| (piperidin-1-ylmethyl)-amide (3) | 33 | 100 | 33 | 100 |
| [(benzyl-methyl-amino)-methyl]-amide (8) | 33 | 100 | 100 | 100 |

Example 4

Table 3 shows the activity of the listed compounds against *M. avium* and *M. tuberculosis* strains as measured by the MIC. In Table 3 the designations 101 and S refer to clinical isolates of *M. avium. M. avium* strain 101 (serotype 1) was provided by Lowell Young (Kuzell Institute for Arthritis and Infectious Diseases, California Pacific Medical Center Research Institute, San Francisco, Calif.). *M. kansasii* S is a clinical isolate from a patient at Veterans Affairs Medical Center, Syracuse, N.Y. In Table 4, ATCC 49601 (serotype 1) is a clinical isolate of *M. avium* from the State University of New York Health Sciences Center, Syracuse, N.Y. It can be seen that the compounds of formula I are more effective against resistant strains than PZA.

TABLE 3

MIC of the Pyrazinamide Analogs Against Various Mycobacteria

| | *M. avium* complex | | *M.* | *M. tuberculosis* | | |
|---|---|---|---|---|---|---|
| Pyrazinoic Acid Amide | 101 | ATCC 49601 | *kansasii* S | ATCC 35801 | ATCC 27294 | ATCC 35828 |
| PZA | >2048 | >2048 | 2048 | 32 | 16 | 2048 |
| 5-Chloro-PZA | 32 | 32 | 32 | 16 | 16 | 8 |
| (morpholin-4-ylmethyl)-amide (4) | >128 | >128 | 128 | 16 | 32 | 16 |
| (pyrrolidin-1-ylmethyl)-amide (1) | >128 | >128 | 128 | 8 | 16 | 2 |
| diethylamino-methyl-amide (2) | 128 | 128 | 128 | 2 | 16 | 1 |
| 5-diethyl-amino-pyrazinoic acid diethylamino-methyl-amide (17) | (>128 | >128 | >128 | 16 | 64 | 16 |

Table 4 shows the activity of selected compounds of formula I against *M. avium* strains. Again, all of the compounds of formula I that were tested had greater activity than PZA.

TABLE 4

MIC of Pyrazinamide Analogs : *M. avium* and *M. kansasii*

| | *M. avium* complex | | |
|---|---|---|---|
| Pyrazinoic Acid Amide | 101 | ATCC 49601 | *M. kansasii* S |
| PZA | >2048 | >2048 | 2048 |
| 5-Chloro-PZA | 32 | 32 | 32 |
| (morpholin-4-ylmethyl)-amide (4) | 128 | >128 | 128 |
| (pyrrolidin-1-ylmethyl)-amide (1) | >128 | >128 | 128 |
| dipropylaminomethyl-amide (9) | 128 | >128 | 128 |
| [(butyl-ethyl-amino)-methyl]-amide (5) | 128 | >128 | >128 |
| [(butyl-methyl-amino)-methyl]-amide (6) | 128 | >128 | 128 |
| (piperazin-1-ylmethyl)-amide (7) | >128 | >128 | >128 |
| dibutylaminoethyl-amide (10) | >128 | >128 | >128 |
| [(benzyl-methyl-amino)-methyl]-amide (8) | 128 | 128 | 128 |

Example 5

FIG. 1 shows the effect of antimycobacterial agents on the number of colony forming units (CFU) of *M. tuberculosis* from macrophages. The graph shows that compound 2 reduced the number of CFU, in comparison with PZA or the control. FIG. 2 shows the results of in vivo experiments in mice. It can be difficult to assess the effectiveness of PZA or a PZA analog in murine models; however, the action in mice of both compounds of formula 1, 1 and 2, and PZA was verified in combination experiments with rifamycin. The addition of PZA to Rifalazil (RLZ, KRM-1648) was effective in reducing infection in a murine model of tuberculosis. PZA has been clearly established to have its greatest effect early in therapy, an observation consistent with clinical experience where the greatest advantage to including PZA is found in the first two months of treatment. In the graph, I and 2 in combination with KRM-1648 (RLZ) clearly showed that these compounds were superior or equivalent to PZA in reducing CFUs. Most significantly these new agents retain activity against PZA resistant organisms in vivo.

Example 6

Table 5 shows that the effect of the compounds of formula I on *M. tuberculosis* is pH-independent.

TABLE 5

Influence of pH on MICs of Pyrazinamide and Morphazinamide Analogs

|  | MS6210 | | ATCC 27294 | | ATCC 35828 | |
| --- | --- | --- | --- | --- | --- | --- |
| Pyrazinamide | pH 6.0 | pH 6.8 | pH 6.0 | pH 6.8 | pH 6.0 | pH 6.8 |
| Pyrazinamide | 33 | >300 | 33 | >300 | >300 | >300 |
| MZA | 100 | 100 | 100 | 100 | 100 | 100 |
| diethylamino-methyl-amide (2) | 100 | 100 | 33 | 100 | 100 | 100 |
| (pyrrolidin-1-ylmethyl)-amide (1) | 100 | 100 | 100 | 100 | 100 | 100 |

Example 7

Activity in vitro and in macrophages. Two of the compounds, pyrazine-2-carboxylic acid diethylaminomethyl-amide (2), and pyrazine-2-carboxylic acid (pyrrolidin-1-ylmethyl)-amide (1) were tested in parallel with PZA and MZA. Results are shown in Table 6. A dramatic difference was found in MICs of PZA when tested under different pH conditions. In contrast, in 7H12 broth, at pH 6.0 and 6.8, MZA, 2 and 3 had the same activity, having MIC of 100 $\mu$g/ml at pH 6 and 8.

PZA-resistant strain even at pH 6.0 (MIC>300), while other three agents were active against this strain at the same level as against the susceptible strains. 1 was also tested, along with PZA and MZA, at pH 5.5 against two *M. tuberculosis* strains. In this experiment, the MICs for a pansusceptible strain were: 50 g./ml for 1, 50 g./ml for MZA, and 25 g./ml for PZA. In an experiment with the PZA-resistant strain the MICs were: 100 g./ml for 1 and MZA, and >300 g./ml for PZA. An examination of the effectiveness of two of the new aminomethylene analogs of PZA in combination with KRM-1648 (RLZ) clearly showed that the new analogs were superior or equivalent to PZA in reducing CFUs in the murine model of tuberculosis. Most significantly these new agents retain activity against PZA resistant organisms in vitro.

Example 8

Effect of pH on activity. Compounds of formula 1 were tested at three pH levels. Results are shown in Table 7. Again, as in experiments with two previously tested 2 and 1, MIC of most of the experimental compounds against a PZA-resistant strain were no higher than that against susceptible strains. In this series of experiments, PZA, as expected, was active against susceptible strains at pH 5.5 and 6.0 only, and not at pH 6.8. At the same time, the activity of MZA and of nine experimental agents at pH 6.8 was no different from or only slightly higher than at pH levels 5.5 and 6.0. It should be noted that at low pH, the MICs of MZA

TABLE 6

MICs (g./ml) of two new compounds compared to PZA and MZA, in the 7H12 BACTEC broth

| | Drug | | | | | | | |
| --- | --- | --- | --- | --- | --- | --- | --- | --- |
| | PZA | | MZA | | 2 | | 1 | |
| Strain | pH 6.0 | pH 6.8 | pH 6.0 | pH 6.8 | pH 6.0 | pH 6.8 | pH 6.0 | pH 6.8 |
| Pansusceptible | 33 | >300 | 100 | 100 | 100 | 100 | 100 | 100 |
| Pansusceptible | 33 | >300 | 100 | 100 | 100 | 100 | 100 | 100 |
| Pansusceptible | 33 | >300 | 100 | 100 | 100 | 100 | 100 | 100 |
| INH-resistant | 33 | >300 | 100 | 100 | 100 | 100 | 100 | 100 |
| PZA-resistant | >300 | >300 | 100 | 100 | 100 | 100 | 100 | 100 |

Another striking difference between PZA and the three other compounds is that PZA did not inhibit growth of the and 9 and 3 against susceptible strains at pH 5.5 and 6.0 were in the same range as those of PZA.

TABLE 7

MICs (g./ml) of PZA amides with susceptible and PZA-resistant strains

| | pH 5.5 | | pH 6.0 | | pH 6.8 | |
| --- | --- | --- | --- | --- | --- | --- |
| Compound | Susc. strains | PZA-res. strain | Susc. strains | PZA-res. strain | Susc. strains | PZA-res. strain |
| PZA | 12.5, 25 | >300 | 25, 50 | >300, >300 | >300, >300 | >300, >300 |
| MZA | 25, 50 | 100, 100 | 25, 50 | 100, 100 | 100, 100 | 100, 100 |
| 9 | 50 | 100 | 25, 50 | 100 | 100, 100 | 100, 100 |
| 7 | 100 | >100 | 50, 100 | >100 | >100, >100 | >100 |
| 3 | 25 | 100 | 25, 25 | 100 | 100, 100 | 100 |
| 8 | 50 | 100 | 50, 100 | 100 | 100, 100 | 100 |
| 3 | 100, 100 | 100 | 100, 100 | 100 | 100, 100 | 100 |
| 16 | 100, 100 | 100 | 100, 100 | 100 | 100, 100 | 100 |
| 11 | 100, 100 | 100 | 100, 100 | 100 | 100, 100 | 100 |
| 15 | 100, 100 | 100 | 100, 100 | 100 | 100, 100 | 100 |

TABLE 7-continued

MICs (g./ml) of PZA amides with susceptible and PZA-resistant strains

| Compound | pH 5.5 | | pH 6.0 | | pH 6.8 | |
|---|---|---|---|---|---|---|
| | Susc. strains | PZA-res. strain | Susc. strains | PZA-res. strain | Susc. strains | PZA-res. strain |
| 12 | 50, 100 | 100 | 100, 100 | 100 | 100, 100 | 100 |
| 14 | 50, 100 | 100 | 100, 100 | 100 | 100, 100 | 100 |

We claim the following:

1. A method for treating diseases involving pyrazinamide-resistant mycobacteria, said method comprising administering to a mammal in need of treatment a therapeutically effective amount of a combination of a rifamycin and a therapeutically effective amount of a compound of formula I, or a pharmaceutically acceptable salt thereof:

I wherein $R^1$ is hydrogen, haloalkyl, or lower alkyl;

$R^2$ and $R^3$ are independently chosen from alkyl, substituted alkyl, cycloalkyl, aryl, substituted aryl, alkylaryl and substituted alkylaryl, or $R^2$ and $R^3$ taken together form a five- or six-membered heterocyclic or substituted heterocyclic ring with nitrogen;

X is hydrogen, halogen, lower alkyl or —$NR^4R^5$; and

$R^4$ and $R^5$ are independently lower alkyl or cycloalkyl, or $R^4$ and $R^5$ taken together form a five- or six-membered heterocyclic or substituted heterocyclic ring with nitrogen.

2. A method according to claim 1 wherein $R^2$ and $R^3$ are independently chosen from alkyl, aryl, and alkylaryl, or $R^2$ and $R^3$ taken together form a five- or six-membered heterocyclic ring chosen from morpholine, piperadine, piperazine, pyrrolidine and substituted piperazine.

3. A method according to claim 1 wherein said compound of formula I is chosen from

1

2

3

5

6

7

8

9

10

-continued

11

12

13

14

15

16

17

4. A method according to claim 1 wherein said compound of formula I

1

5. A method according to claim 1 wherein said compound of formula I

2

6. A method according to claim 1 wherein said compound of formula I is

3

7. A method according to claim 1 wherein said compound of formula I is

4

8. A method according to claim 1 wherein said compound of formula I is

5

9. A method according to claim 1 wherein said compound of formula I is

6

10. A method according to claim 1 wherein said compound of formula I is

7

11. A method according to claim 1 wherein said compound of formula I is

12. A method according to claim 1 wherein said compound of formula I is

13. A method according to claim 1 wherein said compound of formula I is

14. A method according to claim 1 wherein said compound of formula I is

15. A method according to claim 1 wherein said compound of formula I is

16. A method according to claim 1 wherein said compound of formula I is

17. A method according to claim 1 wherein said compound of formula I is

18. A method according to claim 1 wherein said compound of formula I is

19. A method according to claim 1 wherein said compound of formula I is

* * * * *

UNITED STATES PATENT AND TRADEMARK OFFICE
CERTIFICATE OF CORRECTION

PATENT NO. : 6,399,607 B1
DATED : June 4, 2002
INVENTOR(S) : Welch et al.

It is certified that error appears in the above-identified patent and that said Letters Patent is hereby corrected as shown below:

<u>Title page,</u>
Item [57], ABSTRACT, replace "and
X is hydrogen, halogen, or lower alkyl;"
with
-- X is hydrogen, halogen, lower alkyl or $-NR^4R^5$; and
$R^4$ and $R^5$ are independently lower alkyl or cycloalkyl, or $R^4$
and $R^5$ taken together from a five- or six-membered
heterocyclic or substituted heterocyclic ring with nitrogen; --

Signed and Sealed this

Eighth Day of October, 2002

*Attest:*

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO.    : 6,399,607 B1
DATED         : June 4, 2002
INVENTOR(S)   : Welch et al.

It is certified that error appears in the above-identified patent and that said Letters Patent is hereby corrected as shown below:

Title page,
Item [57], ABSTRACT, replace "and
                X is hydrogen, halogen, or lower alkyl;"
with
          -- X is hydrogen, halogen, lower alkyl or $-NR^4R^5$; and $R^4$ and $R^5$ are independently lower alkyl or cycloalkyl, or $R^4$ and $R^5$ taken together form a five– or six-membered heterocyclic or substituted heterocyclic ring with nitrogen; --

This certificate supersedes Certificate of Correction issued October 8, 2002.

Signed and Sealed this

Fifteenth Day of April, 2003

JAMES E. ROGAN
*Director of the United States Patent and Trademark Office*